US00PP17160P2

(12) United States Plant Patent
Carruth

(10) Patent No.: US PP17,160 P2
(45) Date of Patent: Oct. 24, 2006

(54) HYBRID TEA ROSE PLANT NAMED 'WEKCRYING'

(50) Latin Name: *Rosa hybrida*
Varietal Denomination: WEKcrying

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/977,282

(22) Filed: Oct. 28, 2004

(51) Int. Cl.
*A01H 5/00* (2006.01)

(52) U.S. Cl. ..... Plt./137

(58) Field of Classification Search ..... Plt./137
See application file for complete search history.

*Primary Examiner*—Anne Marie Grunberg
*Assistant Examiner*—Annette H Para
(74) *Attorney, Agent, or Firm*—Christie, Parker & Hale, LLP

(57) ABSTRACT

A new variety of Hybrid Tea rose suitable for garden decoration, having flowers of even deep pink coloration.

1 Drawing Sheet

Classification: The present invention relates to a new *Rosa hybrida* plant.

Variety denomination: The new plant has the varietal denomination 'WEKcrying'.

BACKGROUND OF THE INVENTION

This invention relates to a new and distinct variety of Hybrid Tea Rose. It has as its seed parent the variety known as 'ARObipy' (U.S. Plant Pat. No. 6,714) and as its pollen parent the variety known as 'POUIman' (U.S. Plant Pat. No. 6,264).

SUMMARY OF THE INVENTION

Among the features which distinguish the new variety from other presently available and commercial rose cultivars known to the inventor are the following combination of characteristics: its suffusion of red pigmentation on the rachis, its even deep pink flower coloration, its undulated nearly round petals, its heavily suffused red pigmentation on the style and its numerous hairs on the style. The plant has an upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKcrying' may be asexually propagated by budding and grafting. The budding and grafting successfully occurred on the plant/rootstock *Rosa hybrida* cv. 'Dr. Huey'.

Comparison with Parents

The new rose may be distinguished from its seed parent, 'ARObipy' by the following combination of characteristics: whereas 'WEKcrying' bears medium size flowers (about 10.3 to about 11.8 cm. in diameter) of even deep pink coloration, 'ARObipy' bears significantly larger flowers (about 13.0 to about 14.0 cm. in diameter) of white coloration. The new variety has an upright medium height growing habit, whereas the seed parent has a significantly taller upright and bushy growing habit.

The new variety may be distinguished from its pollen parent, 'POUIman' by the following combination of characteristics: whereas 'WEKcrying' bears flowers of even deep pink coloration, 'POUIman' bears flowers of currant red to cardinal red coloration. The pollen parent bears glossy foliage, whereas the new variety bears semi-glossy foliage. 'WEKcrying' has an upright medium height growing habit (about 120 to about 150 cm. in height), whereas, 'POUIman' has a significantly shorter upright compact and bushy growing habit (about 80 to about 100 cm. in height).

Comparison with the Closest Commercially Available Cultivar

The new variety may be distinguished from its closest commercially available cultivar, 'WEKchrisg', by the following combination of characteristics: whereas 'WEKcrying' bears flowers of even deep pink coloration, 'WEKchrisg' bears flowers of cerise pink with a cream reverse coloration. 'WEKcrying' has an upright medium height growing habit (about 120 to about 150 cm. in height), whereas 'WEKchris' has a significantly taller, very upright growing habit (about 220 to about 280 cm. in height.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers singly. Flowers are borne on strong medium to long stems (about 34 to about 72 cm.). Outdoors, the plant blooms abundantly and nearly continuously during the growing season. The flowers have a very slight tea fragrance.

BUD

The peduncle is about 2.3 to about 7.9 cm. in length, of average to somewhat heavy caliper (about 0.4 to about 0.6 cm. in diameter), and usually erect to somewhat stiff. It is moderately rough, with some stipitate glands and some hairs and small prickles. Peduncle color is between 144A and 147B sometimes lightly suffused, especially on the side exposed to the sun, with between 187C and 183C.

Before the calyx breaks, the bud is about 1.6 to about 2.5 cm. in diameter at the widest point, about 1.9 to about 2.8 cm. in length, and pointed to somewhat ovoid in shape. The surface of the bud bears few foliaceous appendages, very few stipitate glands and many hairs, usually with slender entire foliaceous parts extending beyond the tip of the bud about ¼ or more of its length. Bud color is between 146A and 147B sometimes moderately suffused, especially on the side exposed to the sun, with between 187A and 183A.

The sepals are about 3.1 to about 5.1 cm. in length and about 0.7 to about 1.2 cm. in width at the widest point. The outer surface color of the sepal is between 146A and 147B sometimes moderately suffused, especially on the side exposed to the sun, with between 187A and 183A. The inner surface color of the sepal is between 138B and 137B and covered with fine wooly tomentum; sepal margins are lined with some stipitate glands and hairs.

As the petals open (after the calyx breaks), the bud is about 2.4 to about 2.9 cm. in diameter at the widest point, about 2.5 to about 3.5 cm. in length, and moderately ovoid to somewhat globular in form. The color of the under and upper surfaces of the newly opened petals is between 60A and 64A. At the point where the petal attaches, there is a moderately large zone of between 1C and 150C.

BLOOM

When fully open, the bloom ranges from about 10.3 to about 11.8 cm. in diameter. Petalage is double with about 29 to 36 petals and about 2 to 4 petaloids irregularly arranged. When partially open, the bloom form is moderately globular to somewhat cupped, and the petals are moderately tightly spiraled to somewhat cupped with petal edges moderately reflexed outward. When fully open, the bloom form is more cupped, and the petals are loosely cupped to moderately undulated with petal edges moderately reflexed outward.

PETALS

The substance of the petals is moderately heavy and of medium thickness, with upper surfaces somewhat satiny to moderately shiny and under surfaces very shiny. The outer petals are nearly rounded in shape with rounded apices. The inner petals are broadly rounded to somewhat obviate in shape with rounded apices. The petals are about 4.5 to about 5.9 cm. in length and about 3.9 to about 5.8 cm. in width at the widest point. Petal margins are entire.

NEWLY OPENED FLOWER

The under and upper surface color of the outer, intermediate and inner petals is between 57A and 61B. At the point where the petal attaches, there is a moderately large zone of between 4D and 2D.

The general tonality of the newly opened flower is between 57A and 61B.

THREE-DAY-OLD FLOWER

The under and upper surface color of the outer and intermediate petals is between 57B and 61C. At the point where the petal attaches, there is a moderately large zone of between 4D and 2D.

The under and upper surface color of the inner petals is between 57A and 61B.

The general tonality of the three-day-old flower is between 57B and 61C.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 90) and are arranged regularly about the pistils; a few are mixed with petaloids. The filaments are of moderately long length (about 0.5 to about 1.8 cm.), most with anthers. Filaments are between 6D and 5D in color sometimes lightly suffused with near 53D. The anthers are somewhat small for the class and all open approximately at the same time. Anther color is between 16C and 11C when immature and between 163A and 200B at maturity. Pollen is somewhat abundant.

FEMALE REPRODUCTIVE ORGANS

Pistils vary in number (average about 125). The styles are moderately even, somewhat long in length (about 0.6 to about 1.1 cm.), average in caliper, and moderately loosely separated. Stigma color is between 20C and 19B. Style color is between 1D and 2D usually heavily suffused with near 53A. The styles are usually covered with several hairs. Ovaries are usually all enclosed in the calyx.

Hips have not been observed on this variety when grown in Upland, Calif.

FOLIAGE

The compound leaves are usually comprised of three to five or more leaflets and are borne abundantly. The five-leaflet leaves are about 10.3 to about 15.0 cm. in length and about 9.2 to about 13.0 cm. in width at the widest point, moderately leathery to somewhat crisp in texture, and semi-glossy in finish. The terminal leaflets are about 5.0 to about 6.9 cm. in length and about 3.3 to about 5.2 cm. in width at the widest point, shaped moderately oval to somewhat ovate with acute to somewhat acuminate apices and mostly round to sometimes somewhat acute bases. Their margins are usually simply serrate.

The upper surface color of the mature leaf is between 147A and 146A. The under surface color of the mature leaf is between 147B and 147C. The upper surface color of the young leaf is between 146A and 146B, sometimes moderately suffused with between 183B and 187A. The under surface color of the young leaf is between 147B and 146B, sometimes moderately suffused with between 183B and 187A.

The rachis is moderately light in caliper and somewhat rough. The upper side is deeply grooved with some hairs and stipitate glands on the edges of the grooves. The under side of the rachis is somewhat rough with few small prickles. The rachis color is between 147B and 147C sometimes moderately suffused, especially on the young leaves with between 183B and 187A.

The stipules are about 1.3 to about 2.2 cm. in length and of medium width (about 0.5 to about 1.0 cm.) with medium length straight points that usually turn out at an angle of more than 45 degrees and sometimes recurve toward the stem. The stipules color is between 146A and 146B.

The petiole is about 0.6 to about 0.9 cm. in length and about 0.1 to about 0.2 cm in diameter at the widest point. The petiole color is between 147B and 147C sometimes moderately suffused, especially on the young leaves with between 183B and 187A.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright medium height growing habit (about 120 to about 150 cm. in height and about 50 to about 72 cm. spread at the widest point), with full branching. It displays moderately vigorous growth and the canes are of medium to somewhat heavy caliper for the class.

The color of the major stems is between 146C and 146B. They bear many large prickles that are about 0.6 to about 1.2 cm. in length. The large prickles are almost straight and angled slightly downward with a very long somewhat narrow oval base; prickle color is between 166C and 174B. The major stem bears no small prickles.

The color of the branches is between 146B and 147B. They bear many large prickles which are of similar size and shape to the large prickles on the major stems; prickle color is between 160B and 162C sometimes lightly suffused near the base with between 187C and 183C. The branches bear no small prickles.

The color of the new shoots is between 144B and 147B sometimes lightly suffused with between 187A and 183A. They bear many large prickles which are of similar size and shape to the large prickles on the major stems; prickle color is between 145B and 149C usually heavily suffused near the base with between 187A and 187B. The shoots bear some small prickles of similar shape and coloration.

I claim:

1. A new and distinct Hybrid Tea rose plant of the variety substantially as described and illustrated herein.

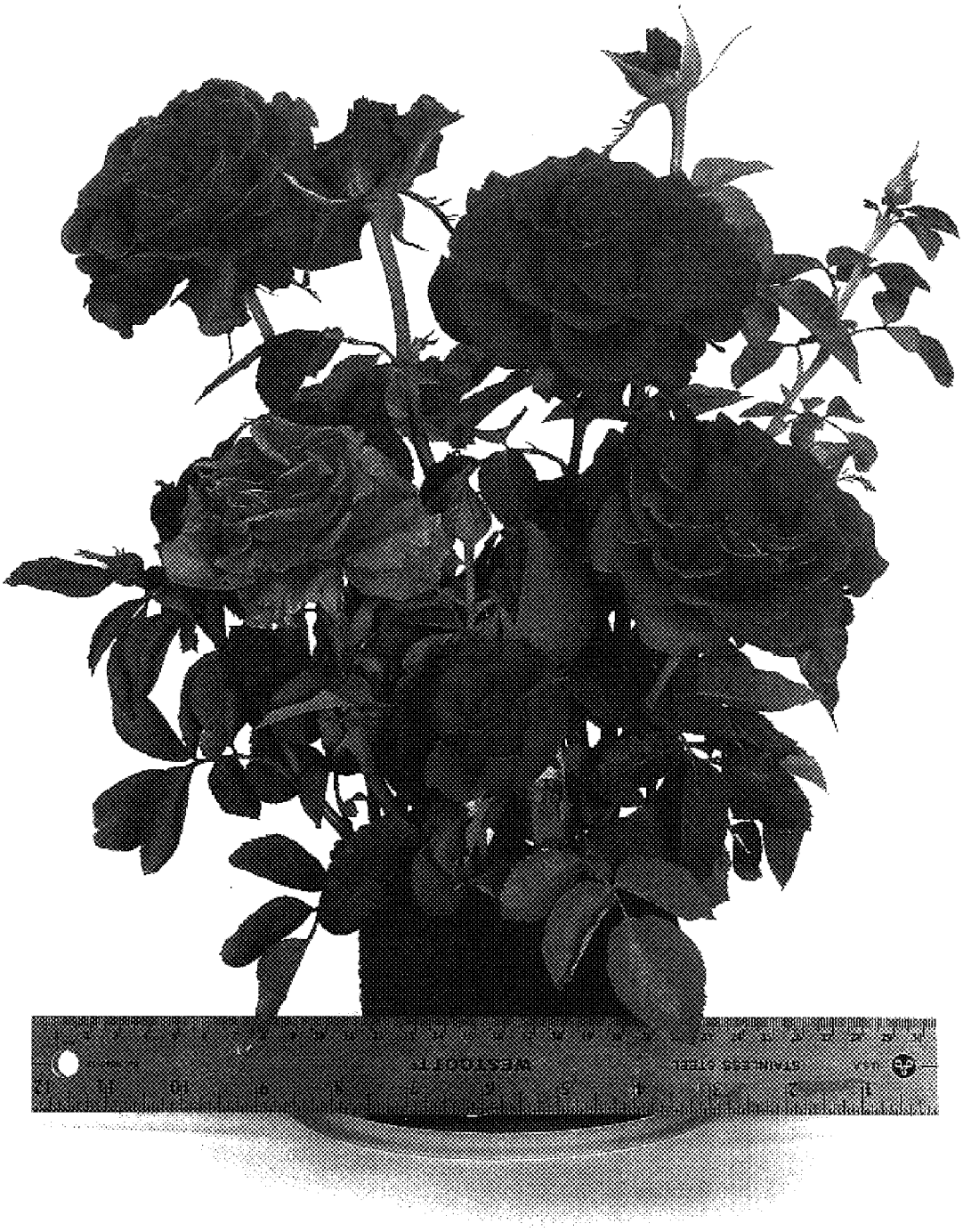

* * * * *